United States Patent [19]

Massaroli

[11] 3,992,543
[45] Nov. 16, 1976

[54] (PYRIDYL-3)-METHYL 2-(p-CHLOROPHENOXY-PHENOXY) PROPIONATE AND USE AS A HYPOLIPEMISING DRUG

[75] Inventor: Giangiacomo Massaroli, Milan, Italy

[73] Assignee: Poli Industria Chimica S.p.A., Milan, Italy

[22] Filed: Nov. 11, 1975

[21] Appl. No.: 631,180

[30] Foreign Application Priority Data
Nov. 20, 1974 Italy.................................. 29614/74

[52] U.S. Cl............................ 424/263; 260/295.5 R
[51] Int. Cl.².............. A61K 31/395; C07D 213/55

[58] Field of Search................... 260/295.5; 424/263

[56] References Cited
UNITED STATES PATENTS

| | | | |
|---|---|---|---|
| 3,622,587 | 11/1971 | Carlson et al................ | 260/295.5 R |
| 3,723,446 | 3/1973 | Scherm et al................ | 260/295.5 R |

*Primary Examiner*—Alan L. Rotman
*Attorney, Agent, or Firm*—Ostrolenk, Faber, Gerb & Soffen

[57] ABSTRACT

(Pyridyl-3)-methyl 2-(p-chlorophenoxy-phenoxy) propionate has interesting properties in reducing cholesterolemia, lipidemia and triglyceridemia, in doses 10 times lower than ethyl p-chlorophenoxy-isobutyrate.

5 Claims, No Drawings

(PYRIDYL-3)-METHYL 2-(p-CHLOROPHENOXY-PHENOXY) PROPIONATE AND USE AS A HYPOLIPEMISING DRUG

This invention relates to (pyridyl-3)-methyl 2-(p-chlorophenoxy-phenoxy)-propionate of (pyridyl-3)-methyl of formula (I)

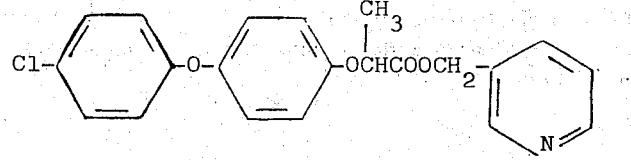

and its preparation. This compound possesses interesting hypocholestereolemising hypolipemising properties, and the invention therefore also relates to pharmaceutical compositions containing the compound (I) as their active principle.

It has been found, in particular, that the oral administration of the compound (I) for 10 consecutive days to rats on normal diet and its oral administration for 5 consecutive days to rats fed with the hypercholesterolic diet of Tensho et al. (J. Pharm. Soc. Jap. 1972, 92, 879) enables the cholesterolemia, the lipidemia and the triglyceridemia to be reduced to the same extent as the reductions obtainable with doses of ethyl p-chlorophenoxy-isobutyrate 10 times greater. Administration occurs by the oral route, in the form of capsules or tablets containing 20–100 mg of active element, at a daily dosage of 100–500 mg.

The compound according to the present invention may be obtained by esterifying 2-(p-chlorophenoxy-phenoxy) propionic acid with 3-pyridylmethanol, using the well-known methods for preparing esters from an acid, from one of its salts or from one of its functional derivatives, and from an alcohol or its derivative.

In particular, in addition to esterification catalysed by strong mineral acids and molecular sieves, the reaction of salts (metallic or of tertiary organic bases) of 2-(p-chlorophenoxy-phenoxy) propionic acid with the 3-halogenomethylpyridines in preferably polar solvents such as alcohols, ketones, cyclic ethers, simple aliphatic amides and the like may be used.

The 2-(p-chlorophenoxy-phenoxy) propionic acid functional derivatives used may, for example, be its halides, which are reacted in apolar solvents with 3-hydroxymethylpyridine in the presence of halogen acid subtracting substances such as metallic carbonates and tertiary organic bases. Other possible derivatives are its lower alkyl esters or its imidazolide, which are reacted with 3-hydroxymethylpyridine in the presence of catalytic quantities of alkaline alkoxides.

The following examples illustrate the preparation of the compounds according to the present invention, without in any way limiting its scope.

EXAMPLE 1

A solution of 2-(p-chlorophenoxy-phenoxy) propionyl acid chloride (obtained from 10 g of acid 0.0343 moles) in 25 ml of anhydrous toluene is dripped at 30° C into a solution of 11.1 g (0.102 moles) of 3-hydroxymethylpyridine in 50 ml of anhydrous toluene. The mixture is agitated at 30° C for 3 hours, the 3-hydroxymethylpyridine hydrochloride is filtered, the filtrate is concentrated at reduced pressure and the residue is crystallised from isopropyl ether.

11 g are obtained, representing a yield of 84%. M.p. 61°–2° C.

Elementary analysis: For $C_{21}H_{18}ClNO_4$ Calculated: C, 65.71; H, 4.72; N, 3.64. Found: C, 65.48; H, 4.73; N, 3.57.

MeOH: 267 m$\mu$ (E1% 102)
$\lambda_{MAX}$: 277 m$\mu$ ('' 76.8)

EXAMPLE 2

A solution of 2-(p-chlorophenoxy-phenoxy) propionic acid chloride (obtained from 10 g of acid, ie 0.0343 moles) in 30 ml of toluene are added at 30° C under agitation to a solution of 3.82 g (0.035 moles) of 3-hydroxymethylpyridine and 6.77 g (0.067 moles) of triethylamine in 50 ml of anhydrous toluene. The triethylamine hydrochloride is filtered after 3 hours of agitation at 30° C, the filtrate is concentrated at reduced pressure and the residue is crystallised from isopropyl ether, obtaining 7.88 g (60%) of product. M.p. 61°–2° C.

EXAMPLE 3

A mixture of 10 g (0.0312 moles) of ethyl 2-(p-chlorophenoxy-phenoxy) propionate, 10.2 g (0.0935 moles) of 3-hydroxymethylpyridine and 0.175 g of potassium tert-butylate is heated to 50°–60° C/15–20 mm for 3–8 hours until the reaction is complete. The alkali is neutralised with acetic acid, the mixture is diluted with water, the oily product is extracted in ether, the extract is washed with water and dried over sodium sulphate, and after evaporating the solvent the aforementioned procedure is repeated to give 6.5 g (54.5%) of product. M.p. 61°–2° C.

EXAMPLE 4

A solution of 6.1 g (0.0372 moles) of 3-chloromethylpyridine hydrochloride in 20 ml of dimethylformamide is dripped into a solution of 10.5 g (0.0372 moles) of 2-chlorophenoxy-phenoxy) propionic acid and 7.5 g (0.074 moles) of triethylamine in 50 ml of dimethylformamide. The mixture is agitated for 3 hours at 30° C, diluted with water, the oily product is extracted in ether, and the process continued as described in example 3. 7.2 g (51%) of product are obtained with a m.p. of 61°–2° C.

What we claim is:
1. (Pyridyl-3)-methyl 2-(p-chlorophenoxy-phenoxy)-propionate of the formula (I)

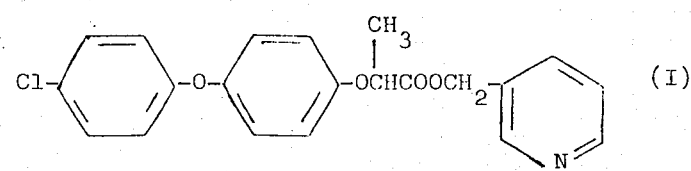 (I)

2. Pharmaceutical composition with hypocholesterolemising and/or hypolipemising effective amount of the compound as claimed in claim 1 as its active principle.

3. Pharmaceutical composition as claimed in claim 2 wherein the amount of the compound is 20 to 100 mg.

4. Pharmaceutical composition as claimed in claim 3 in the form of a tablet.

5. Pharmaceutical composition as claimed in claim 3 in the form of a capsule.

* * * * *